United States Patent [19]

Takizawa et al.

[11] 4,270,845
[45] Jun. 2, 1981

[54] LASER APPARATUS FOR OPERATIONS

[75] Inventors: Toshiaki Takizawa, Tokyo; Kazumasa Takeuchi, Chofu; Takashi Togo, Tokyo, all of Japan

[73] Assignee: Mochida Pharmaceutical Co., Ltd., Tokyo, Japan

[21] Appl. No.: 703,744

[22] Filed: Jul. 9, 1976

[30] Foreign Application Priority Data

Jan. 7, 1976 [JP] Japan .................................. 51-947
Jan. 12, 1976 [JP] Japan ................................ 51-2123

[51] Int. Cl.$^3$ ............................................. G02B 5/08
[52] U.S. Cl. .............................. 350/299; 128/303.1; 219/121 L
[58] Field of Search ................ 350/299, 301, 285; 331/94.5 PE, 94.5 D, 94.5 C, 94.5 G, DIG. 1; 219/121 L, 121 LM; 128/303.1

[56] References Cited

U.S. PATENT DOCUMENTS

| | | | |
|---|---|---|---|
| 3,481,340 | 12/1969 | McKnight | 350/299 |
| 3,528,424 | 9/1970 | Ayres | 331/DIG. 1 |
| 3,696,230 | 10/1972 | Friedrich | 219/121 L |
| 3,720,213 | 3/1973 | Hobart et al. | 219/121 L |
| 3,826,998 | 7/1974 | Kindl et al. | 331/94.5 D |
| 3,828,788 | 8/1974 | Krasnov et al. | 128/303.1 |
| 3,913,582 | 10/1975 | Sharon | 128/303.1 |

OTHER PUBLICATIONS

Griesheim, (Messer Griesheim) High-Performance $CO_2$ Gas Laser, GL 350A, advertising brochure.

*Primary Examiner*—R. A. Rosenberger

[57] ABSTRACT

A laser apparatus for operations comprises a power case containing a power supply, etc., a laser tube container head located over the power case, means for supporting the laser tube container head so as to permit rotation in a horizontal plane and in a manner to enable seesaw motion in a vertical plane, a longitudinally telescoping light guide tube attached longitudinally to the laser tube container head, mirror joints connected with the light guide tube, and a manipulator connected detachably with the mirror joints.

A forced-oil cooled laser apparatus comprises mirror holder electrodes which hold an inner glass tube and an outer transparent pipe coaxially in an airtight manner, and an intermediate electrode, the mirror holder electrodes being provided with discharge gas intake and outlet ports and with cooling oil intake and outlet ports, the discharge gas intake and outlet ports being connected with a vacuum pump and a discharge gas cylinder, the cooling oil intake and outlet ports being connected with a cooler and a compressor.

20 Claims, 8 Drawing Figures

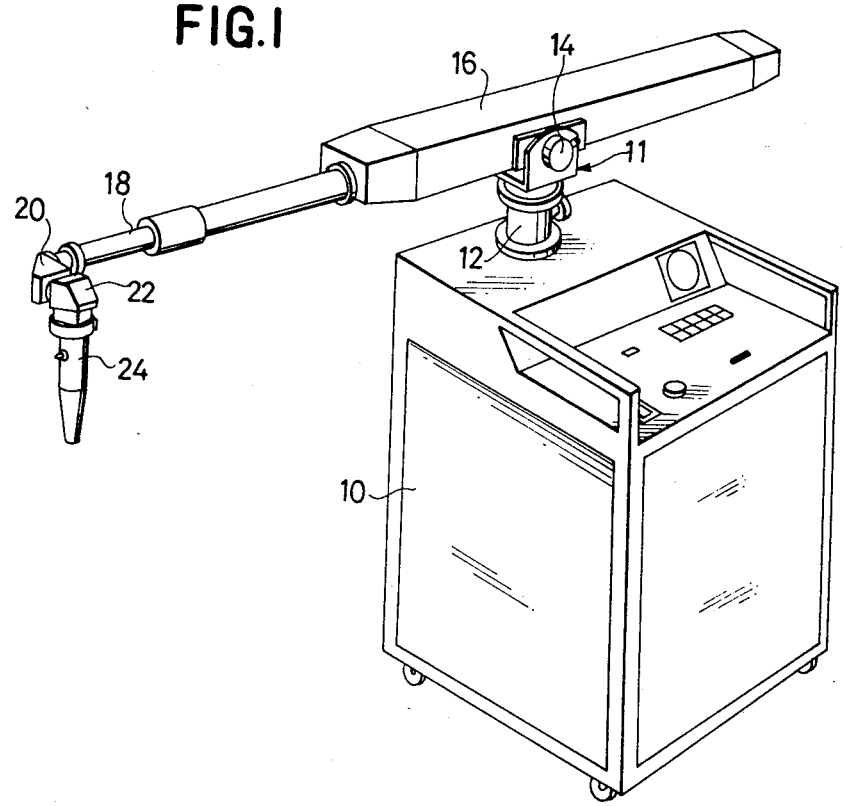
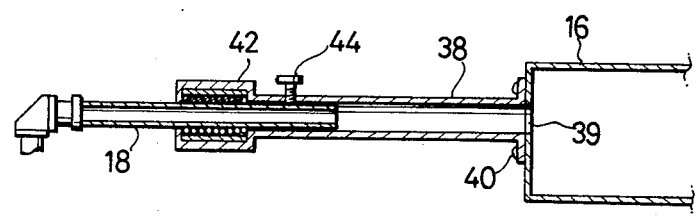

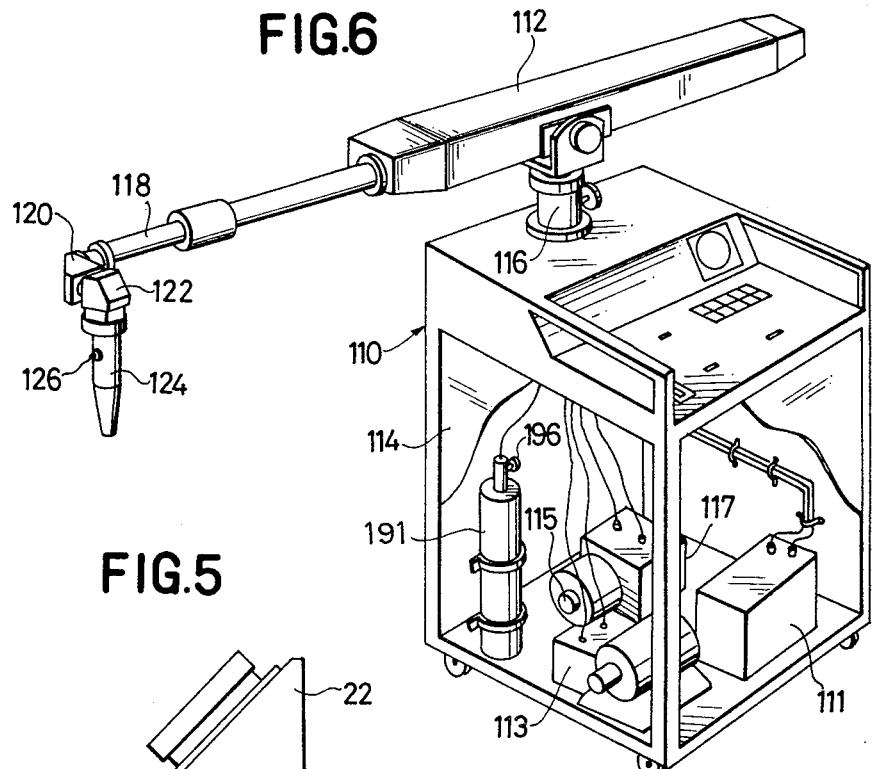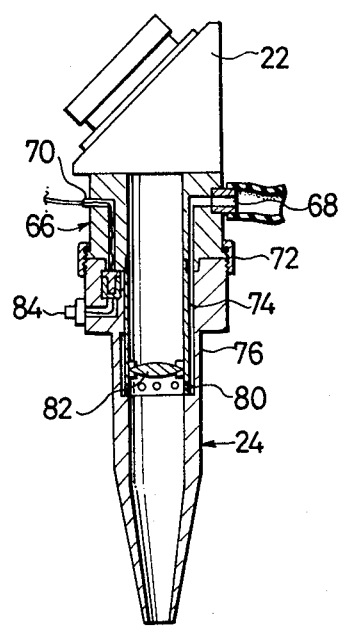

LASER APPARATUS FOR OPERATIONS

BACKGROUND OF THE INVENTION

This invention relates to a laser apparatus for use in operations. Laser apparatus for operations is an apparatus for application of laser light to operations. Since laser light can focus a high energy density on a fine portion, laser apparatus for operations has the following advantages:

(1) Precision operations can be performed.

(2) Operations without contact of metals, etc. with the living body, that is, contactless operations, can be performed.

(3) Bleeding at the time of operation is minimized.

Among laser devices, a $CO_2$ laser is advantageous in that it has a high output power, high efficiency and low production cost. In addition, the $CO_2$ laser has a wavelength of $10.6\mu$ which is well absorbed into the living body, for which reason the $CO_2$ laser is extremely effective for operation purposes such as incision and coagulation.

Fundamentally, as set forth above, laser apparatus for operations have many advantages. However, conventional laser apparatus for operations are considered to be disadvantageous in the following points:

(1) The height of the apparatus itself is too large. If a laser apparatus for operation is too high, it will strike the upper portion of the entrance of a room when moved from one operating room to another and thus causes a problem; and, even in the operating room, it will strike the shadowless light for illumination installed over the operating table, which also causes a problem during an operation.

Laser tube may be installed vertically or horizontally relative to the power case. It is publicly known that the laser output increases as the laser tube becomes longer. It is also publicly known that the laser tube is folded as to lengthen the path for laser light and at the same time to shorten the dimension occupied by the laser tube. In the method of installing laser tube vertically, however, a certain increase in height is unavoidable even by folding the laser tube and thus it has been impossible to eliminate the foregoing drawbacks.

On the other hand, in the method of installing the laser tube over the power case so that the tube is horizontally movable, in order to smooth the operation of the manipulator which comprises a tip end through which laser light comes out, it has been necessary either to construct the laser tube-containing case so that the entire case goes up and down while it is held horizontally, or to render the light guide tube vertically expansible which tube is for conducting laser light to manipulator. Thus the vertical dimension of the apparatus as a whole has unavoidably been large.

(2) Since there are many mirror joints attached to the light guide tube which is for conducting laser light from a laser device to the manipulator, the decrease in output from the manipulator is large. The well-known method for freely conducting laser light is by means of a mechanism in which a mirror is mounted at an inclination of 45° relative to the incident ray and the mirror is rotated 360° about the incident optical axis as an axis of rotation. That is, several mirror joints are combined.

Conventional vertical type or horizontally movable type laser apparatus required at least seven mirror joints. (For example, see Japanese Patent Public Disclosure No. 94182/74 which was laid open to public inspection on Sept. 6, 1974.) Even with only two or three mirror joints, it seems possible to perform operations if operations are simple. However, actual experiments have proved that the operation is inconvenient and not practicable. If as many as seven mirror joints are used, laser light will repeat reflection many times, resulting in the reflection loss being increased by a geometrical progression and the output power from manipulator is greatly decreased.

(3) If the number of mirror joints is many, a precise machining is required, adjustment of optical axis requires longer time, and deviation is liable to be produced on prolonged use. As can be seen from the rule of light reflection, deviation of mirror by an angle of $\theta$ relative to the incident ray would be accompanied by a deviation by $2\theta$ in the direction of reflected ray. Since this doubled deviation will be further increased by geometrical progression because of a deviation of each mirror, an extremely precise machining is required for the adjusting mechanism of each mirror and for a true right angle between the incident side light guide tube and the outgoing side light guide tube in articulation. Further, if, as in conventional apparatus, the light path from laser oscillator to the tip end of the manipulator through which laser light advances is long, there will be an increased deviation of the optical axis.

(4) Conventional laser devices are provided with a laser tube which has a pair of metal electrodes near the ends thereof. The metal electrodes and the glass tube are required to be in close contact with each other, but the difference in their physical properties has made the production of the laser tube difficult.

(5) The output power of a laser device is proportional to the length of the laser tube of the device. To stabilize the output power of a laser tube, it is necessary to maintain the temperature of the tube constant. Conventional laser devices use tap water for cooling the laser tube, which requires piping. However, this not only takes time and labor, but also the presence of a water hose in the operating room obstructs operation and may even cause an unforeseen accident. The output power of a laser device, as set forth above, is affected by the effect of cooling heat generated by the discharge of the laser tube of the device. In this respect, conventional laser devices have a problem in that the temperature of the laser tube varies according to the change in temperature of tap water or the change in its flow rate, thus causing a change in output power of the laser device.

SUMMARY OF THE INVENTION

Accordingly, an object of the invention is to provide a laser apparatus for operations which is superior in operability with a limited height.

Another object of the invention is to provide a laser apparatus for operations which has a minimized output power loss from the manipulator.

Another object of the invention is to provide a laser apparatus for operations whose laser tube can be easily produced.

Another object of the invention is to provide a laser apparatus for operations which has a stable laser output.

Another object of the invention is to provide a laser apparatus for operations which can be moved easily in an operation room.

According to one aspect of the present invention, the above-mentioned objects are achieved by a laser apparatus for operations comprising a power case containing a power supply, etc., a laser tube container head located over said power case, means for supporting said laser tube container head rotatably in a horizontal plane and in a manner to enable seesaw motion in a vertical plane, a longitudinally telescoping light guide tube attached longitudinally to said laser tube container head, a small number of mirror joints connected with said light guide tube, and a manipulator connected detachably with said mirror joints.

The laser apparatus for operations according to this aspect of the present invention is advantageous in that the height of the entire apparatus is low because the light guide tube is provided in the longitudinal direction of the laser tube container head and in that because the number of mirror joints used is small, reflection loss is minimized, easy machining is made possible, adjustment of the optical axis does not require much labor and trouble and once the adjustment is made deviation is difficult to occur for a long period.

According to another aspect of the present invention, the above-mentioned object is achieved by a forced-oil cooled laser apparatus including mirror holder electrodes which hold an inner glass tube and an outer transparent pipe coaxially in an airtight manner, and an intermediate electrode, said mirror holder electrodes being provided with discharge gas intake and outlet ports and with cooling oil intake and outlet ports, said discharge gas intake and outlet ports being connected with a vacuum pump and a discharge gas cylinder, said cooling oil intake and outlet ports being connected with a cooler and a compressor.

The forced-oil cooled laser apparatus of this aspect of the present invention is advantageous in that since the mirror holder electrodes serve as both mirror holder and electrode, the production of the device is easy and in that since the inner glass tube is cooled by cooling oil which is recycled by means of a cooler and a compressor both built in the laser apparatus, not only is there obtained a stable laser output, but also the laser apparatus can be moved easily because a cooling water piping is not needed.

Other and further objects, features and advantages of the invention will be appear more fully from the following description.

BRIEF DESCRIPTION OF THE DRAWINGS

FIG. 1 is a perspective view illustrating the laser apparatus for operations according to the present invention;

FIG. 3 is a sectional plan view of the light guide tube;

FIG. 5 is a sectional plan view of the manipulator partially in section; P FIG. 6 is a broken away perspective view illustrating an embodiment of the forced-oil cooled laser apparatus according to the present invention;

DETAILED DESCRIPTION OF THE PREFERRED EMBODIMENTS

Figure 2:
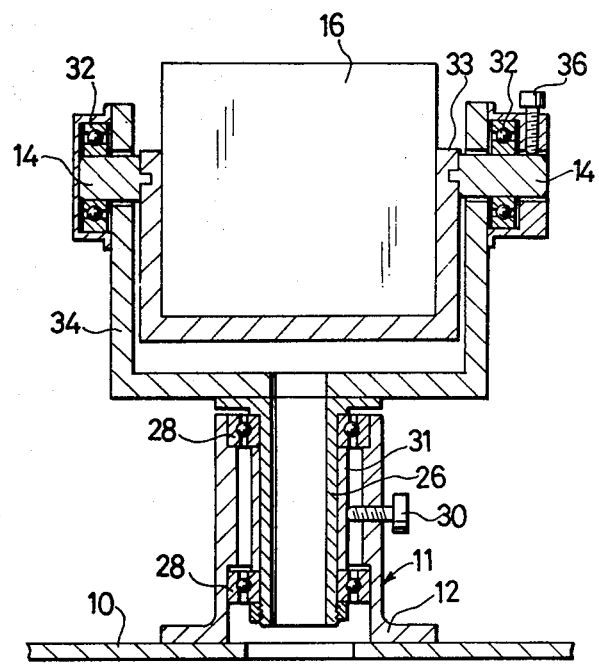
FIG. 2 is a sectional elevational view of the laser tube container head supporting means.

Details of the laser apparatus for operations according to the present invention are explained below while reference is made to the accompanying drawings.

FIG. 1 is a perspective view illustrating an embodiment of the laser apparatus for operations according to the present invention. A power case 10 containing a power supply etc. is provided thereabove with a supporting means 11 for supporting a laser tube container head 16. The laser tube container head supporting means 11 is provided with a flanged sleeve 12 which has bearings for rotation of the laser tube container head 16 in a horizontal plane and also with side shafts or trunions 14 whereby the laser tuber container head 16 for the housing laser tube, etc. is supported in a manner to enable an up-and-down seesaw motion. The laser tube container head 16 has a light guide tube 18 which is longitudinally fitted therein and which effects a stroke motion to the right and left. The light guide tube 18 is connected to a manipulator 24 through a mirror joint 20 which rotates about the light guide tube 18 as an axis of rotation and a mirror joint 22 which rotates about an axis at a right angle to the light guide tube 18. The manipulator 24 is operated manually by the operator when effecting operation.

The laser tube container head 16 is supported by the side shafts 14 at its center of gravity when the light guide tube 18 occupies the leftmost position in the drawing. Consequently, when the light guide tube 18 has withdrawn to the rightmost position, there will be a somewhat larger moment on the right side with the side shafts 14 serving as a fulcrum so that the manipulator on the left side when released goes up and is held at the lifted condition. That is, even when released in operation, the manipulator 24 never goes down, which is safe for the living body, but it is slowly lifted and held at the lifted condition and thus an easy handling of manipulator is available.

FIG. 2 is a sectional view illustrating the internal structure of the flanged sleeve 12 and of the side shafts 14. A main shaft 26 is borne by two ball bearings 28 which are fixed to the sleeve 12, the sleeve being secured to the power case 10, so that the main shaft 26 can rotate 360° freely in a horizontal plane. A lock screw 30 threaded into the sleeve 12 is used for applying a pressure to the main shaft 26 through a sleeve 31 and thereby locking the main shaft at a desired angle of rotation. The laser tube container head 16 is fixed to the side shafts 14 through a support 33 and the side shafts 14 are mounted rotatably in a support plate 34 through two right and left ball bearings 32. Consequently, the laser tube container head 16 can effect an up-and-down seesaw motion in a vertical plane with the side shafts 14 serving as the fulcrum. A lock screw 36 is used for holding down the side shaft 14 directly or indirectly and thereby fixing the laser tube container head 16 at a desired angle.

FIG. 3 is a longitudinal, sectional elevation view illustrating the section of the light guide tube 18. A bearing tube 38 is attached to a laser light irradiation window 39 of the laser tube container head 16. In order that the optical axis of laser light and the central axis of the bearing tube 38 may be concentric with each other, an adjusting mechanism 40 is provided between the right end of the bearing tube 38 and the laser tube container head 16. The adjusting mechanism 40 may be, for example, of the construction in which three screws are tightened through a thick, ring-like spacer while adjusting the tightening force so as to adjust the gradient of the axis of the bearing tube 38. The light guide tube 18 can effect a right and left axial stroke motion through a bearing for 42 which is provided at the left end of the bearing tube 38. A lock screw 44 is used for locking the light guide tube 18 at a desired position.

Figure 4:
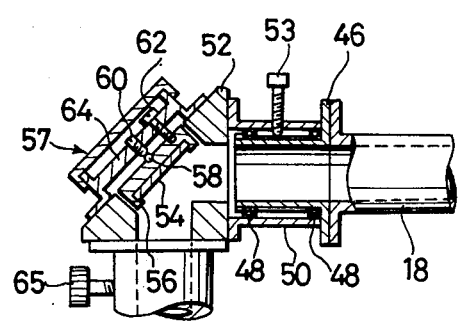
FIG. 4 is a sectional elevational view of the mirror joint.

FIG. 4 is a partially sectional, elevational view fully illustrating the section of the mirror joint 20. A bearing shaft 46 that is fixed to the light guide tube 18 is held in a bearing housing 50 through a bearing 48, with the bearing housing 50 being fixed to a right-angled triangular block 52. The block 52 is locked with a lock screw 53 at a desired angle of rotation relative to the light guide tube 18. A mirror holder 56 which holds a reflecting mirror 54 is attached to the triangular block 52 by means of an optical axis adjusting mechanism 57. That is, the mirror holder 56 is pushed by a machine screw 60 through a steel ball 58 and at the same time is pulled by three machine screws 62, and thus it is fixed at a certain position. Adjustment of the optical axis can be made by adjusting the three machine screws 62. In other words, the incident optical axis can be bent exactly 90° by setting the reflecting mirror 54 at 45° relative to the incident optical axis. Also, by moving the reflecting mirror forward or backward by adjusting the machine screw 60, adjustment can be made so that the incident optical axis will pass through the center of the incident light guide tube and the outgoing optical axis through the center of the outgoing light guide tube of the manipulator 24. Whether the adjustment of optical axis is sufficient or not can be determined by checking whether the outgoing laser light becomes eccentric or not when a mirror holding case 64 is rotated while it is kept in contact with the oblique side of the right-angled triangular block 52. The mirror joint 22 has the same structure and function as those of the mirror joint 20. Also, a lock screw 65 has the same structure and function as the lock screw 53.

FIG. 5 is a partially sectioned elevational view illustrating a section of the manipulator 24. A coupling adapter 66 fixed to the mirror joint 22 has a gas inlet 68 and two electrodes 70, and it also has a coupling thread 72 for connection with the manipulator 24. The coupling thread 72 enables the manipulator 24 to be attached to and detached from the coupling adapter 66 in several seconds, which is convenient in changing the manipulator. Since the manipulator 24 which approaches the incision part of the living body must be sterilized before operation, it is a great advantage that the manipulator 24 can be detached for sterilization. The manipulator 24 is composed of an inner pipe 74 and an outer pipe 76, with the inner pipe 74 being provided at its lower end with a visible and infrared ray lens capable of simultaneously condensing $CO_2$ laser light and HeNe laser light, for example, ZnSe lens 82. Gas from the gas inlet 68 passes between the inner pipe 74 and the outer pipe 76 and is blown off from a gas blow-off port 80 which is provided below the lens 82 at the lower end of the inner pipe 74, so that the surface of the expensive ZnSe lens is always kept clean by the blown-off gas. Upon coupling of the manipulator 24 with the coupling adapter 66, the electrodes 70 are connected with a push-button switch 84 mounted in the manipulator 24, so that the opening and closing operation of the beam shutter as will be described hereinafter can be done in the operator's hand by pushing the push-button switch 84. According to the present invention, the gas inlet 68 and the electrodes 70 are positioned at upper portions of the manipulator 24 and therefore they do not become an obstacle when a surgeon performs an operation holding the manipulator 24 with his hand, and thus the manipulator 24 is superior in operability. If it is desired that the position of the manipulator 24 be fixed and laser light be directed to only one point upon which guide light strikes, it can be accomplished by tightening the lock screws 30, 36, 44, 53 and 65. If it is desired that the manipulator 24 effect only linear motion, it can be accomplished by releasing only lock screw 44 and tightening the other lock screws 30, 36 53 and 65. Further, if the lock screw 65 alone is released and the other lock screws 30, 36, 44 and 53 are tightened, the manipulator can perform only a rotational motion in a certain plane.

FIG. 6 is a partially broken away perspective view illustrating an embodiment of the forced-oil cooled laser apparatus 110 of the present invention. A laser tube container head 112 is fixed over a power case 114 by means of a supporting means 116 that permits rotation in a horizontal plane and in a manner to enable seesaw motion in a vertical plane, with the power case 114 containing a power source 111, a vacuum pump 113, a compressor 115, etc. In the laser tube container head 112 is axially fitted a light guide tube 118 capable of effecting a telescopic motion. The other end of the light guide tube 118 is connected with a manipulator 124 throught mirror joints 120, 122. The manipulator 124 has a push-button switch 126, which when depressed causes a laser light to be emitted from the tip end of the manipulator as will be described hereinafter.

Figure 7:
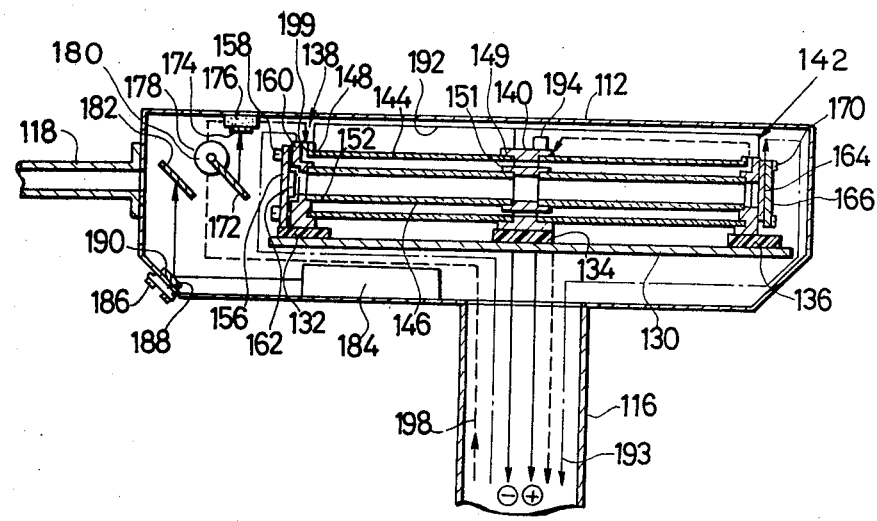
FIG. 7 is a sectional elevational view of the laser tube container head.

FIG. 7 is a sectional elevational view illustrating the internal structure of the laser tube container head 112 which is used in the forced-oil cooled laser apparatus 110 of the present invention.

Figure 8:
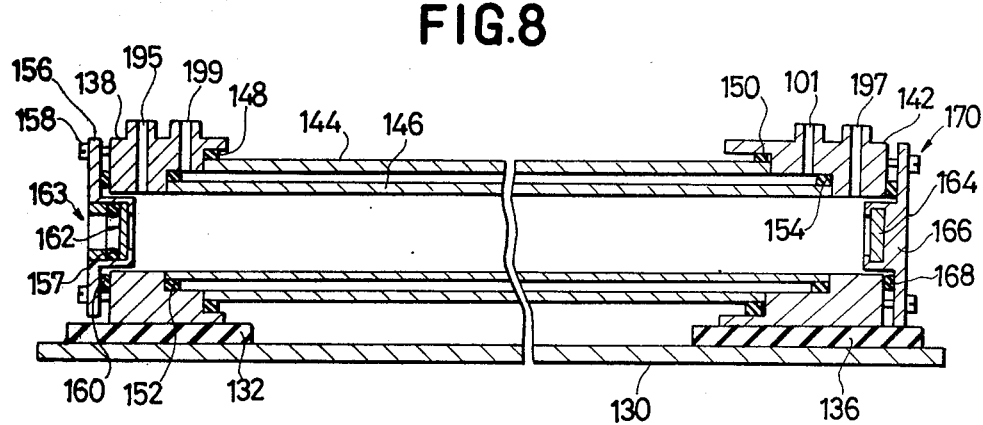
FIG. 8 is an enlarged sectional elevational view illustrating both ends of the laser tube container head.

FIG. 8 is an expanded sectional elevational view showing both ends of the laser tube container head 112. The laser tube container head 112 is provided internally with a resonator base 130 on which are fixed a left mirror holder negative electrode 138, an intermediate positive electrode 140 and a right mirror holder negative electrode 142 through insulating plates 132, 134 and 136. By these mirror holder electrodes are held an outer transparent pipe e.g., an acryl pipe 144 and an inner glass tube e.g., a Pyrex glass tube 146 in an airtight manner, which airtightness ia assured by O-rings 148, 150, 152, 154, 149 and 151. A mirror holder 156 is held on the left mirror holder negative electrode 138 by means of an optical axis adjusting mechanism 158 in an airtight manner through an O-ring 160. The optical axis adjusting mechanism 158 is composed of, for example, three-point adjusting screws. By adjusting the tightening force of each screw there can be made adjustment of the optical axis of an output side mirror 162 which is held on the mirror holder 156 through an O-ring 157 (FIG. 8). In the same way, a mirror holder 166 which holds a reflection side mirror 164 is held on the right mirror holder negative electrode 142 by means of an optical axis adjusting mechanism 170 in an airight manner through an O-ring 168.

$CO_2$ laser light which has been transmitted through the output side mirror 162 and has come out of an output opening 163 is reflected by a beam shutter 172 (FIG. 7) and irradiated upon an output detector 174. The output detector 174, which is fixed to a heat sink 176, converts the output power of the laser light into an electric signal and sends the latter signal to a servo control circuit for stabilization of the laser output power. To be more specific, when the laser output exceeds the preset value the discharge current is reduced to decrease the laser output power; on the contrary, when the laser output becomes lower than the preset value, the discharge current is increased to increase the laser output. Thus the output can be stabilized to any value at all times. This servo control circuit may be of the type utilizing a thyristor or of the type which employs a motor to slide a slide transformer.

When the push-button switch 126 of the manipulator 124 is depressed, a shaft 180 of a rotary solenoid 178 turns 45°, causing the beam shutter 172 to spring up, so that the laser light can go straight. The laser light then goes through an infrared transmitting mirror e.g., Ge filter 182, further goes through the light guide tube 118 and mirror joint 120 and is emitted from the tip end of the manipulator 124. The Ge filter 82 is a filter with an antireflection film of a wavelength of $10.6\mu$ and made of germanium. A red laser light with a wavelength of 6328Å from He-Ne laser means 184 is bent perpendicularly in an upward direction by a reflector 190 which is held on a mirror holder 188 having a three-point adjusting mechanism 186 and is then reflected by the Ge filter 182 which is positioned at an angle of 45° to the optical axis $CO_2$ laser beam and thus advance along the same optical axis as $CO_2$ laser beam which has passed through the Ge filter 182.

The left mirror holder negative electrode 138 and the right mirror holder negative electrode 142 both are connected through an electric wire 192 to the minus terminal of the power supply 111, while the intermediate positive electrode 140 is connected through an electric wire 194 to the plus terminal of the power supply 111. The interior of the Pyrex tube 146 is vacuum-exhausted with the vacuum pump 113 such as a rotary pump, whereupon a mixed gas of He, Ne and $CO_2$ from a high-pressure bomb 191, the flow rate of which has been adjusted by a control valve 196 (FIG. 6), is taken in from a discharge gas intake port 195 and taken out from an outlet port 197 as shown by the alternate long and short dash line 193. Into the spacing between the transparent acryl pipe 144 and the Pyrex glass tube 146 is conducted, as shown by the dotted line 198, an insulating oil from a cooling oil intake port 199 which insulating oil has been sent from the compressor 115 to the heat sink 176 where it has cooled the sink, and the oil is then taken out from an outlet port 101. The insulating oil is cooled to a fixed temperature by means of a cooler 117 which is housed in the proper case 114 and is then recycled between the laser tube and the cooler at a fixed flow rate by means of the compressor 115.

In the forced-oil cooled laser apparatus of the present invention, as set forth above, the mirror holder electrodes serve as both mirror holder and electrode. Therefore, unlike conventional laser apparatus, the laser apparatus of the present invention dispenses with the difficult glass work for enclosing metal electrodes in a glass pipe and can be easily assembled using a standardized transparent acryl pipe and a standardized Pyrex glass tube. Among acryl pipes, the one which is transparent is used in the most preferred embodiment of the present invention. This results in making the discharge condition visible from the outside. In the force-oil cooled laser apparatus of the present invention, moreover, cooling of the apparatus is accomplished by recycling an insulating oil at a fixed temperature only at a fixed flow rate unlike conventional laser apparatus which employs a water flow, so that there is no danger of the discharge becoming unstable because of a current flow in water or of an electric shock, nor is there an inconvenience of tap water piping in the operating room.

In this embodiment there is shown a straight tube type laser device in which the laser tube is in the form of a straight line. To increase the laser output power, however, a folded type laser tube may be used. The folded type laser tube results from the art of shortening the dimension of the laser tube case by bending a long straight laser tube in the form of V or N letter with an articulated reflector.

Since certain changes may be made in the above apparatus without departing from the scope of the invention herein involved, it is intended that all matter contained in the above description or shown in the accompanying drawings shall be interpreted as illustrative and not in a limiting sense.

What is claimed is:

1. A laser apparatus for operations comprising a power case containing a power supply, a laser tube container head mounted directly on and located over the power case, means for supporting the laser tube container head in a manner to enable seesaw motion in a vertical plane about a horizontal axis, a longitudinally telescoping light guide device attached to the laser tube container head, the light guide device being movable between fully extended and fully retracted positions, mirror joints connected with the light guide device and a manipulator connected with the mirror joints, the laser tube container head being supported by means located at the center of gravity thereof when the light guide device is in the fully extended position whereby when the light guide device is in the fully retracted position the means for supporting the laser tube container head will act as a fulcrum and there will be a downward force exerted by the laser tube container head on the side of the means for supporting the laser tube container head that is remote from the manipulator such that the manipulator with the light guide device will always tend to move in an upwardly direction and will tend to remain in the elevated position absent a force being applied thereto in the downward direction.

2. A laser apparatus for operations as claimed in claim 1 wherein said means for supporting said laser tube container head has a single rotatable vertical axis on said power case which does not move in a horizontal plane and a bearing means for supporting said laser tube container head, said mirror joints and said manipulator approximately at the center of gravity of said last three mentioned components for rotation around said vertical axis in a horizontal plane.

3. A laser apparatus for operations as claimed in claim 1 wherein said light guide device includes a bearing tube and a light guide tube longitudinally fitted into said bearing tube to effect a stroke motion right and left, said means for supporting said laser tube container head supporting the gravity center of said laser tube container head, said light guide device, said mirror joints and said manipulator for up-and-down seesaw motion of said laser tube container head in a vertical plane when said light guide tube occupies its most extended position.

4. A laser apparatus for operations as claimed in claim 2 wherein said means for supporting said laser tube container head has a setting lock member for locking said laser tube container head at a desired angle in a horizontal plane and permitting movement only in a vertical plane.

5. A laser apparatus for operations as claimed in claim 3 wherein said means for supporting said laser tube container head has a setting lock member for locking said laser tube container head at a desired angle in a vertical plane and permitting movement only in a horizontal plane.

6. A laser apparatus for operations as claimed in claim 1 wherein said mirror joint includes a right-angled triangular block and a mirror holder for holding a reflecting mirror, said mirror holder having a small adjustment mechanism for directing said reflecting mirror and being in close contact with an oblique side of said right-angled triangular block and attaching said mirror holder to said right-angled triangular block as the desired position.

7. A laser apparatus for operations as claimed in claim 1 wherein said manipulator is detachably connected to said mirror joint.

8. A laser apparatus for operations as claimed in claim 1 wherein said manipulator consists of an inner pipe and an outer pipe to form a double construction.

9. A laser apparatus for operations as claimed in claim 8 wherein said manipulator includes a coupling adapter secured to said mirror joint and a manipulator body threaded to said coupling adapter.

10. A laser apparatus for operations as claimed in claim 9 wherein said coupling adapter has a gas inlet for introduction of gas into said manipulator of double construction and a pushbutton switch for controlling the laser output.

11. A laser apparatus for operations as claimed in claim 10 wherein said laser tube is comprised of an inner glass tube and a concentric outer pipe and said apparatus further includes a pair of outboard mirror holder electrodes and an intermediate electrode for holding said inner glass tube and said outer pipe coaxially in an airtight manner.

12. A laser apparatus for operations as claimed in claim 11 wherein said mirror holder electrodes have a discharge gas intake port and an outlet port, and a cooling oil intake port and an outlet port.

13. A laser apparatus for operations as claimed in claim 12 wherein said apparatus further includes a vacuum pump and a discharge gas cylinder communicated with said discharge intake and outlet ports.

14. A laser apparatus for operations as claimed in claim 12 wherein said apparatus further includes a cooler and a compressor communicated with said cooling oil intake and outle ports.

15. A laser apparatus for operations as claimed in claim 11 wherein at least one of said mirror holder electrodes has an optical axis adjusting mechanism for supporting said mirror holder.

16. A laser apparatus for operations as claimed in claim 11 wherein said apparatus further comprises a detector for use in stabilizing the laser light output.

17. A laser apparatus for operations as claimed in claim 11 wherein said apparatus has a beam shutter member that is rotatable in response to the operation of said push-button switch, said beam shutter member having a first position that reflects the outgoing laser light beam to an output detector for indicating the output of the laser and a second position that passes the outgoing laser light beam and a visible laser light beam therethrough along a common axis, there being further included an infrared transmitting mirror for reflecting said visible laser light beam to said common axis.

18. A laser apparatus for operations as claimed in claim 11 wherein said outer pipe is made of methyl methacrylate.

19. A laser apparatus for operations as claimed in claim 11 wherein said apparatus has a folded type laser tube.

20. A laser apparatus for operations as claimed in claim 1 wherein said mirror joints connected with said light guide device has at least two rotatable axes positioned at right angles to each other.

* * * * *